US00PP23762P2

(12) United States Plant Patent
Smith

(10) Patent No.: US PP23,762 P2
(45) Date of Patent: Jul. 23, 2013

(54) ***CHRYSANTHEMUM* PLANT NAMED 'CIFZ0003'**

(50) Latin Name: *Chrysanthemum×morifolium*
Varietal Denomination: CIFZ0003

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 34 days.

(21) Appl. No.: 13/385,184

(22) Filed: Feb. 6, 2012

(51) Int. Cl.
*A01H 5/00* (2006.01)

(52) U.S. Cl.
USPC ..... Plt./287

(58) Field of Classification Search
USPC ..... Plt./287
See application file for complete search history.

*Primary Examiner* — Kent L Bell
(74) *Attorney, Agent, or Firm* — Joshua L. Price

(57) ABSTRACT

A new *Chrysanthemum* plant named 'CIFZ0003' particularly distinguished by the small red-purple decorative inflorescences, medium green foliage, medium ball-shaped plant habit, and a natural flowering season response of late September.

1 Drawing Sheet

Latin name of the genus and species of the plant claimed: *Chrysanthemum×morifolium.*

Varietal denomination: 'CIFZ0003'.

BACKGROUND OF THE NEW PLANT

The present invention comprises a new *Chrysanthemum*, botanically known as *Chrysanthemum×morifolium*, and hereinafter referred to by the variety name 'CIFZ0003'.

'CIFZ0003' is a product of a planned breeding program. The new cultivar has small red-purple decorative inflorescences, medium green foliage, medium ball-shaped plant habit, and a natural flowering season response of late September.

'CIFZ0003' originates as a natural whole plant mutation of an unpatented plant designated '05-M166'. 'CIFZ0003' was discovered and selected by the inventor as a single flowering plant within a large population of the parent cultivar, grown massed in pots outdoors in a controlled breeding program in Alva, Fla. in April 2008. The parent cultivar '05-M166' has a purple inflorescence color and a natural flowering season response that is a few days slower than 'CIFZ0003'.

The first act of asexual reproduction of 'CIFZ0003' was accomplished when vegetative cuttings were propagated from the initial selection in May 2008 in a greenhouse in Alva, Fla.

BRIEF SUMMARY OF INVENTION

Horticultural examination of plants grown from cuttings of the plant initiated in May 2008, and continuing thereafter, has demonstrated that the combination of characteristics as herein disclosed for 'CIFZ0003' are firmly fixed and are retained through successive generations of asexual reproduction.

'CIFZ0003' has not been observed under all possible environmental conditions. The phenotype may vary significantly with variations in environment such as temperature, light intensity, and day length.

Plant Breeder's Rights for this cultivar were applied for in Canada on Feb. 24, 2011, No. 11-7177 and at Community Plant Variety Office on Mar. 30, 2011, No. 2011/0788. 'CIFZ0003' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0003' with colors being as true as possible with an illustration of this type. The photographic drawing shows a flowering potted plant of the new variety and a close-up of a flower.

DETAILED BOTANICAL DESCRIPTION

The plant descriptions, measurements and aforementioned photograph were taken outdoors in Gilroy, Calif. in early November 2011. These plants were grown outdoors in gallon pots and were approximately 12 weeks of age.

Color references are made to The Royal Horticultural Society Colour Chart (R.H.S.) 2001.

TABLE 1

DIFFERENCES BETWEEN THE NEW VARIETY 'CIFZ0003' AND A MOST SIMILAR VARIETY

| | 'CIFZ0003' | 'Gedi Two Ped' (U.S. Plant Pat. No. 14,501) |
|---|---|---|
| Inflorescence color: | More red-purple | Little more purple |
| Inflorescence diameter: | Smaller | Larger |
| Quantity of disc florets: | Fewer | Many more |
| Plant habit/size: | Smaller overall/rounder | Little larger/more upright |

TABLE 1-continued

DIFFERENCES BETWEEN THE NEW VARIETY 'CIFZ0003' AND A MOST SIMILAR VARIETY

| | 'CIFZ0003' | 'Gedi Two Ped' (U.S. Plant Pat. No. 14,501) |
|---|---|---|
| Black cloth flowering response: | Faster | Slower |
| Natural flowering season response: | Slower | Faster |

Plant:
- *Form, growth and habit.*—Herbaceous garden-type, stems upright and outwardly spreading, freely branching.
- *Plant height.*—10.0 cm.
- *Plant height (inflorescence included).*—12.0-13.0 cm.
- *Plant width.*—24.0-26.0 cm.

Roots:
- *Number of days to initiate roots.*—About 4 days at about 22 degrees C.
- *Number of days to produce a rooted cutting.*—4-6 days at 22 degrees C.
- *Type.*—Fine, fibrous, free branching.
- *Color.*—RHS N155B but whiter.

Foliage:
- *Arrangement.*—Alternate.
- *Immature, leaf color, upper surface.*—RHS 137A but a little lighter.
- *Lower surface.*—Closest to RHS 137B but appears lighter due to hairs.
- *Mature, leaf color, upper surface.*—Closest to RHS 137A.
- *Lower surface.*—Closest to RHS 137B but appears lighter due to hairs.
- *Length.*—2.9-3.1 cm.
- *Width.*—2.4-2.6 cm.
- *Shape.*—Ovate.
- *Base shape.*—Attenuate.
- *Apex shape.*—Mucronulate.
- *Margin.*—Palmately lobed; irregularly incised; slightly serrulate.
- *Texture, upper surface.*—Bifid T-shaped hairs.
- *Lower surface.*—Bifid T-shaped hairs.
- *Color of veins, upper surface.*—RHS 138B.
- *Color of veins, lower surface.*—Indistinct.
- *Petiole color.*—RHS 138B.
- *Length.*—0.6-0.7 cm.
- *Diameter.*—0.2 cm.
- *Texture.*—Bifid T-shaped hairs.

Stem:
- *Quantity of main branches per plant.*—About 10.
- *Color of stem.*—RHS 138A.
- *Length of stem.*—About 7.0 cm.
- *Diameter.*—0.3 cm.
- *Length of internodes.*—0.5-1.0 cm.
- *Texture.*—Bifid T-shaped hairs.
- *Color of peduncle.*—RHS 138A.
- *Length of peduncle.*—3.5-5.5 cm.
- *Peduncle diameter.*—0.1 cm.
- *Texture.*—Bifid T-shaped hairs.

Inflorescence:
- *Type.*—Compositae, solitary decorative inflorescences; borne terminally above foliage, ray florets arranged acropetally on a capitulum.
- *Quantity of inflorescences per plant.*—About 100.
- *Lastingness of individual blooms on the plant.*—A little less than 6 weeks from first color showing.
- *Fragrance.*—Slightly spicy.

Bud (just when opening/showing color):
- *Color.*—Closest to RHS 77B but more grey.
- *Length.*—0.7-1.2 cm.
- *Width.*—0.8-1.1 cm.
- *Shape.*—Oblate.

Immature inflorescence:
- *Diameter.*—2.5-2.9 cm.
- *Color of ray florets, upper surface.*—Between RHS 70A and RHS 71A.
- *Lower surface.*—Closest to RHS 77B.

Mature inflorescence:
- *Diameter.*—3.1-3.5 cm.
- *Depth.*—1.3-1.5 cm.
- *Total diameter of disc.*—0.2-0.3 but only on very mature inflorescences.
- *Receptacle height.*—0.2-0.3 cm.
- *Receptacle diameter.*—0.3-0.4 cm.

Ray florets:
- *Average quantity of florets.*—About 100 in numerous whorls.
- *Color of florets, upper surface.*—RHS 70A to RHS 70B.
- *Lower surface.*—RHS 77B but greyer.
- *Length.*—1.4-1.6 cm.
- *Width.*—0.3-0.4 cm.
- *Shape.*—Oblong.
- *Apex shape.*—Praemorse.
- *Margin.*—Entire.
- *Texture, upper surface.*—Papillose.
- *Lower surface.*—Papillose.

Disc florets:
- *Average quantity of florets.*—2-4.
- *Color of florets.*—RHS 1C.
- *Length.*—0.2-0.3 cm.
- *Width.*—0.1 cm.
- *Shape.*—Tubular, elongated.
- *Apex shape.*—Acute, 5 pointed.

Phyllaries:
- *Quantity.*—About 30.
- *Color, upper surface.*—RHS 137B.
- *Lower surface.*—RHS 137C.
- *Length.*—0.4-0.5 cm.
- *Width.*—0.15 cm.
- *Shape.*—Lanceolate.
- *Apex shape.*—Acute.
- *Base.*—Fused.
- *Margins.*—Entire.
- *Texture, upper surface.*—Glabrous.
- *Lower surface.*—Bifid T-shaped hairs.

Reproductive organs:
- *Pistil.*—1, found on both types of florets.
- *Length.*—0.3-0.4 cm.
- *Style color.*—RHS 155C.
- *Style length.*—0.2-0.3 cm.
- *Stigma color.*—RHS 1A.
- *Stigma shape.*—Bi-parted.
- *Ovary color.*—RHS 155C.
- *Ovary length.*—0.1 cm.
- *Ovary width.*—0.1 cm.
- *Stamens.*—4, found only on the disc florets.
- *Color of filaments.*—RHS 155C.
- *Length filaments.*—0.3 cm.

*Anther color*.—RHS 13B.
*Anther length*.—0.1 cm.
*Anther shape*.—Oval.
*Pollen amount*.—Scarce.
*Color of pollen*.—About RHS 15C.

What is claimed is:

1. A new and distinct variety of *Chrysanthemum* plant named 'CIFZ0003' substantially as illustrated and described herein.

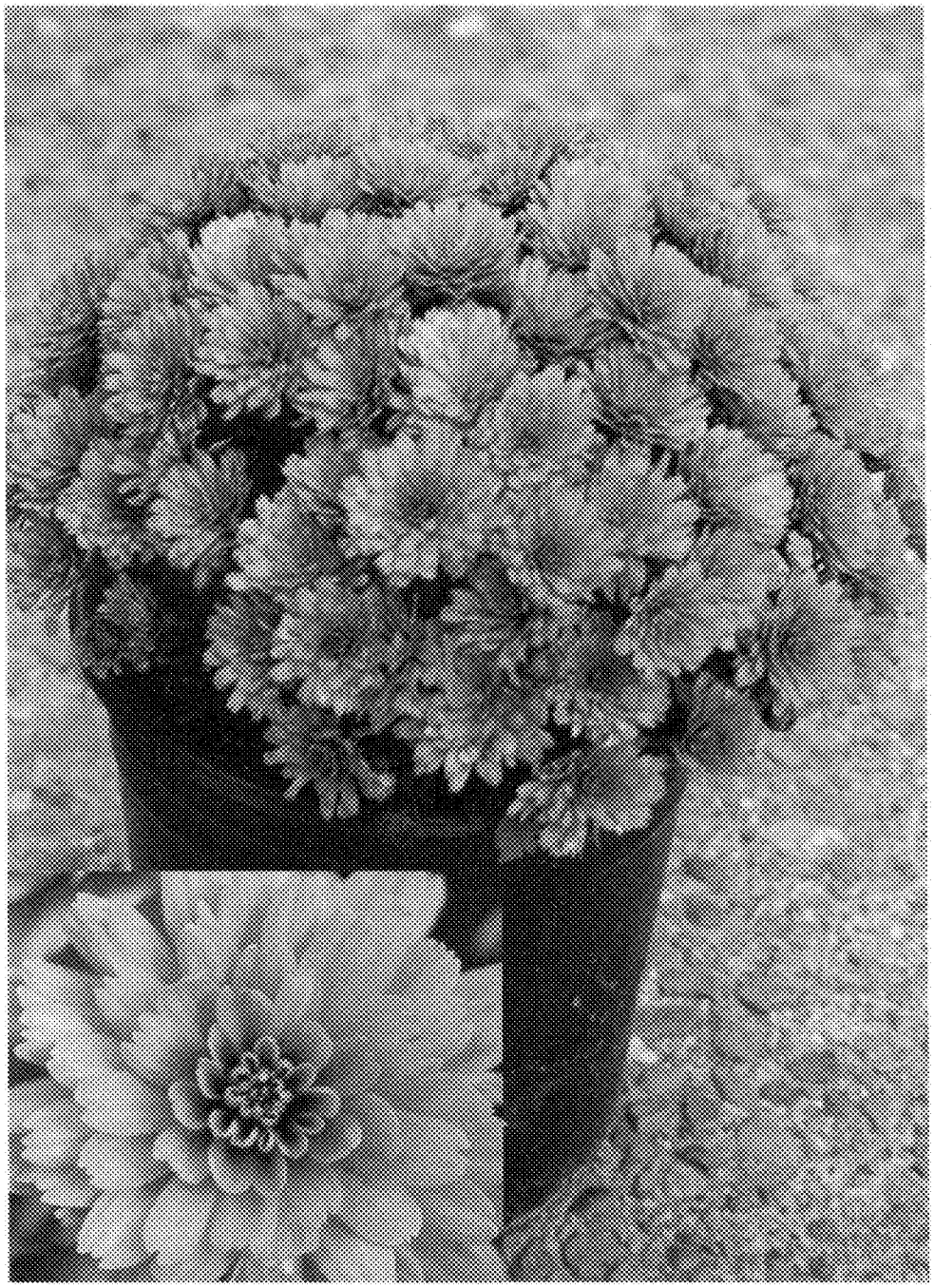

* * * * *